US006479070B1

(12) United States Patent
Cain et al.

(10) Patent No.: US 6,479,070 B1
(45) Date of Patent: Nov. 12, 2002

(54) COMPOSITIONS CONTAINING PINOLENIC ACID AND ITS USE AS A HEALTH COMPONENT

(75) Inventors: Frederick William Cain, Wormerveer (NL); Preyesh Parmar, Sharnbrook Bedford (GB); Jonathan Richard Powell, Sharnbrook Bedford (GB); Julia Sarah Rogers, Sharnbrook Bedford (GB)

(73) Assignee: Unilever Patent Holdings, Vlaardingen (NL)

( * ) Notice: Subject to any disclaimer, the term of this patent is extended or adjusted under 35 U.S.C. 154(b) by 0 days.

(21) Appl. No.: 09/672,487

(22) Filed: Sep. 29, 2000

(30) Foreign Application Priority Data

Sep. 30, 1999 (EP) .............................................. 99307752
Oct. 13, 1999 (EP) .............................................. 99308062

(51) Int. Cl.$^7$ ........................ A61K 47/00; A23D 7/06; A23D 9/00; C08K 5/58; C08K 5/06
(52) U.S. Cl. ...................... 424/439; 424/94.6; 426/603; 426/604; 524/181; 524/182; 524/351; 524/352; 524/375
(58) Field of Search ................................ 424/94.6, 439; 426/603, 607, 604; 524/181, 182, 351, 352, 375

(56) References Cited

U.S. PATENT DOCUMENTS 4,425,371 A * 1/1984 Stratmann et al. .......... 426/603
5,567,751 A * 10/1996 Hoch ........................ 524/181

FOREIGN PATENT DOCUMENTS

FR 2 756 465 6/1998

OTHER PUBLICATIONS

Sugano et al, British Journal of Nutrition, 72:775–783 (1994).
Matsuo et al, Prostaglandins Leukotrienes and Essential Fatty Acids, 55(4):223–229 (1996).
Derwent Publications, AN 1986–117166, XP002134074 (JP 61–058536.

* cited by examiner

Primary Examiner—Christopher R. Tate
Assistant Examiner—Kailash C. Srivastava
(74) Attorney, Agent, or Firm—Morgan, Lewis & Bockius LLP

(57) ABSTRACT

Pinolenic acid can be used in the form of a food supplement, a pharmacentical composition or as part of a food composition as anti-inflammatory agent. The pinolenic acid used herefore suitably is applied as a natural product, or as a concentrate with more than 28 wt % pinolenic acid. The concentrates can be made by a process, wherein an enzymic hydrolysis on a glyceride material is performed.

6 Claims, 1 Drawing Sheet

The graph below Fig. 2 demonstrates that pinolenic acid also decreases the production of Intracellular adhesion molecule (ICAM), which is another marker of inflammation.

COMPOSITIONS CONTAINING PINOLENIC ACID AND ITS USE AS A HEALTH COMPONENT

It is well known that pinolenic acid (=5,9,12 C18:3 fatty acid i.e. a fatty acid with 18 C atoms having three double bonds in the positions 5, 9 and 12) is present in e.g. pine nut oil or fractions thereof in amounts of up to about 25 wt %. (cf e.g. J Am Oil Chem Soc 1998, 75, p.45–50). It is also known that pine nut oil (and thus pinolenic acid) can be applied in food products (cf e.g. Fr 2 756 465 wherein the use of a concentrate with 15% pinolenic in food additives is disclosed. The presence of pinolenic acid provides a hypolipemic effect to the composition). Further the prior art indicates that pinolenic acid derivatives have a number of health benefits. E.g. WO 9843513 discloses that nail files can be coated with pinolenic acid and that this inhibits the occurrence of infections upon use of the files.

According to JP 61238729 pine oil can be used as anticholesterimic agent. Other documents wherein health effects of pinolenic acid are disclosed are:

Japanese Patent Application 61058536, wherein a very generic activity beneficial for human health is disclosed; Sugano c.s in Brit J. of Nutr 72 (1994) 775–783, wherein hypocholesterolaemic effects, effects on ADP-induced platelet aggregation, on aortic prostacylic production and on blood pressure are reported while Matsuo discloses in Prostagl, Leukotrienes and Essential fatty Acids 55 (1996) 223–229 effects on CD-4"-lymphocytes and on CD8+-subsets.

However none of the prior art documents indicate that pinolenic acid could have anti-inflammatory properties. We performed a study in order to find compounds with anti-inflammatory properties. This study resulted in the finding that pinolenic acid can be used as an anti-inflammatory agent. Therefore our invention concerns in the first instance the use of a composition, preferably in the form of a food supplement, a pharmaceutical composition or a food composition, comprising 1.5 to 100 wt %, preferably 5 to 80 wt %, most preferably 10 to 50 wt % of pinolenic acid and wherein the composition is used as an anti-inflammatory agent.

An efficient way to administer an effective dose of the anti-inflammatory component is to administer a food supplement to the consumer. Therefore our invention also concerns food supplements with anti-inflammatory properties comprising a composition with 1.5 to 100 wt %, preferably 5 to 80 wt %, most preferably 10 to 50 wt % of pinolenic acid, which supplements preferably comprise a component, containing pinolenic acid, in encapsulated form in a food grade encapsulating material. The component containing the pinolenic acid can be selected from free fatty acid mixtures or from glyceride mixtures or from mixtures hereof. The glyceride mixture used preferably is derived from pine nut oil or concentrates thereof, in particular a concentrate of pine nut oil with a content of pinolenic acid of more than 28 wt % is applied. The encapsulating material can be any food grade material that according to prior art methods can be used in encapsulated food products.

According to another embodiment concentrates of pinolenic acid, wherein the concentrate comprises 28 to 60 wt % of pinolenic acid, 10 to 60 wt % of linoleic acid, 5 to 52 wt % of oleic acid, while its trans plus saturated fatty acid content is less than 10 wt % are also part of the invention. In these concentrates the pinolenic acid and other fatty acids can be present as free acids and/or in the form of mono- and/or di- and/or triglycerides. These concentrates can be applied in food products or they first can be blended with other components in order to achieve a structuring effect upon use in a food product. Therefore part of the invention are also blends of a composition (A), containing pinolenic acid and one or more other components (B), wherein the composition (A) comprises 1.5 to 100 wt % of pinolenic acid, while the other components (B) are selected from glycerides comprising linoleic acid and/or oleic acid and/or trans acids and/or saturated fatty acids while (A) and (B) have a preselected composition and are present in such ratios that the final blend contains:

0 to 70 wt %, preferably 25 to 65 wt % (trans plus saturated fatty acids), while the trans content preferably is less than 10 wt %;

1.5 to 60 wt % of pinolenic acid and 25 to 85 wt % of (linoleic plus oleic acid).

These blends can be applied beneficially in food products as healthy fat compounds.

Preferred blends are blends wherein composition (A) is a concentrate according to the invention and wherein the components (B) are selected from the group consisting of:

i) liquid oils, such as soybean oil; sunflower oil; rape seed oil and cotton seed oil ii) cocoa butter or cocoa butter equivalents iii) palm oil or fractions thereof iv) enzymically made fats v) fish oils or fractions thereof vi) conjugated linoleic acid or enriched isomer mixtures thereof vii) gamma linoleic acid or enriched mixtures thereof viii) hardened liquid oils ix) mixtures of one or more of components i) to viii).

Above blends preferably display solid fat contents measured by NMR-pulse on non stabilized fats of: N20=1–80, preferably 5–45 N35 less than 20, preferably less than 10, most preferably less than 5. Non stablised meaning that the fat was melted at 80° C., cooled to 0° C. and held at 0° C. for 30 min, whereupon the fat was heated to measurement temperature and held thereon for 30 min before measuring the N value. The concentrates according to the invention can be prepared by a process wherein an enzymic hydrolysis or glycerolysis is performed using an enzyme that can discriminate between fatty acids with a delta 5 double bond and other fatty acids. Therefore this process involves the preparation of a concentrate of pinolenic acid having more than 28 wt % pinolenic acid by:

i) reacting a glyceride material containing at least 2 wt % of fatty acid with a $cis^5$ double bond with water or glycerol in the presence of an enzyme capable of discriminating between fatty acids containing a delta double bond and other fatty acids ii) splitting the reaction mixture into a partial glyceride rich component and a fatty acid rich component iii) optionally converting the fatty acid rich component of step ii) to triglycerides by reaction with glycerol in the presence of a suitable enzyme iv) optionally splitting the partial glyceride rich material of step ii) into components that are i) rich in monoglycerides, ii) rich in diglycerides and iii) rich in triglycerides and then optionally converting the partial glycerides i) and ii) into triglycerides by reaction with fatty acids in the presence of a suitable enzyme.

Figure 1:
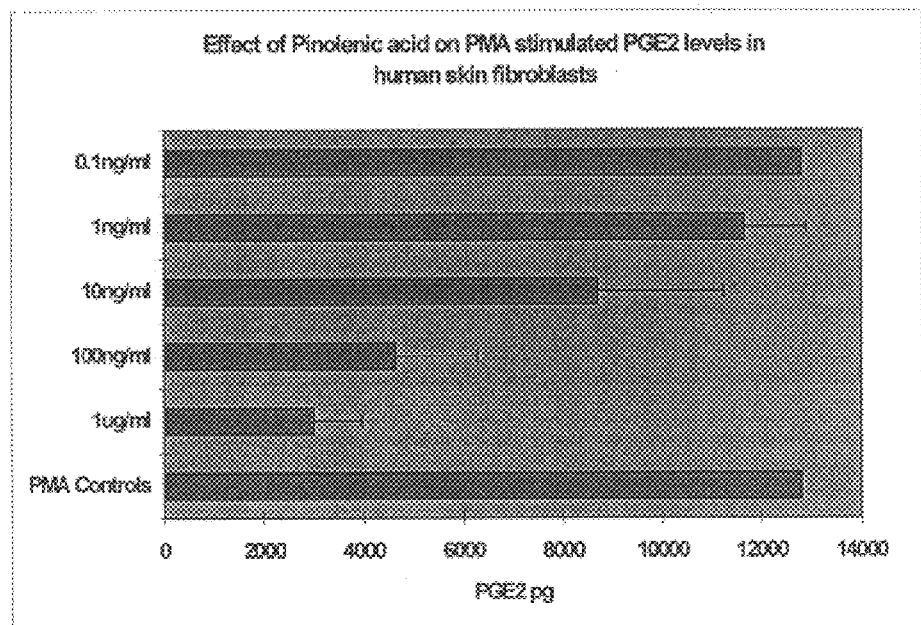
FIG. 1-Effect of Pinolenic Acid on PMA stimulated PGE2 Levels in Human Skin Fibroblasts.
Figure 2:
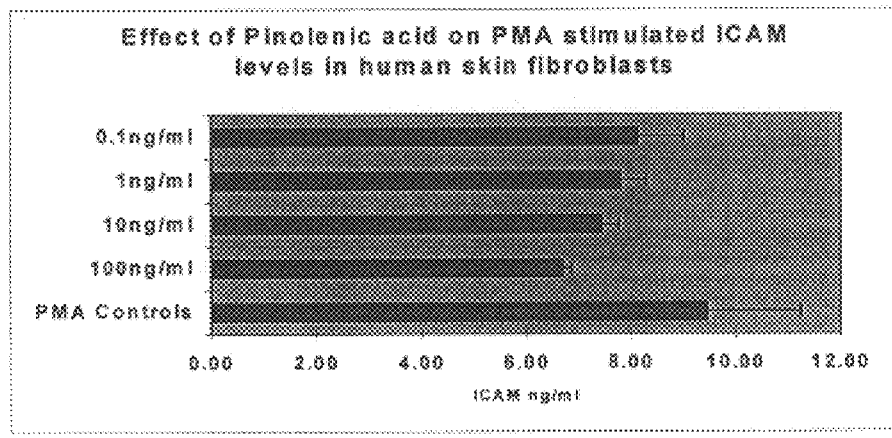
FIG. 2-Effect of Pinolenic Acid on PMA stimulated ICAM Levels in Human Skin Fibroblasts.

It is preferred to use in step i) a glyceride material with a pinolenic acid content of 5 to 30 wt %, preferably 10 to 25 wt %. Examples of such materials are pine nut oils or concentrates thereof.

The enzyme that can be applied in step i) can be selected from the group consisting of *Candida rugosa* lipase; Lipase QL; Lipase SL, Lipase OF; Rhizopus delemar; Rhizopus oryzae and *Geotrichum candidum* B lipase.

The enzyme that suitably can be used in step iii) of our process is Lypozyme IM (a commercial enzyme from NOVO), whereas in step iv) it is preferred to use Lipozyme M (also from NOVO) as the enzyme material.

According to a last embodiment our invention concerns with food products containing pinolenic acid, in particular margarines; low fat spreads; very low fat spreads; bicontinuous spreads; water continuous spreads; confectionery products, such as chocolates, coatings or fillings; ice creams; ice cream coatings; ice cream inclusions; dressings; mayonnaises; sauces; bakery fats; shortenings or cheese containing an effective amount of pinolenic acid to achieve an anti-inflammatory effect upon consumption by the incorporation in the product of a sufficient amount of the concentrate according to the invention or the blend according to the invention.

It is emphasized that the anti-inflammatory effects were determined by in vitro tests wherein the production of intracellular adhesion molecules (=ICAM) and Prostaglandin E2 (=PGE2) production by the human skin fibroblasts and blood vessel endothelials cells (HUVECS) is measured after being induced by the inflammatory modulus PMA. A reduction of the levels of ICAM and PGE2 is indicative for the anti-inflammatory effect.

Primary human foreskin fibroblasts at passage 2 (P2) were seeded into 96-well plates at 10000 cells/well and maintained for 24 hours in an atmosphere of 5% carbon dioxide in Dulbeccos Modified Eagles Medium (DMEM) supplemented with 10% foetal calf serum. Pinolenic acid was added to fresh cell media in ethanol (final concentration 1%) in triplicate and incubated for a further 24 hours. Phorbal myristate acetate (PMA) (Sigma) in ethanol/cell media was added to the media and the cells incubated for a further 24 hours. PMA represents an external stressor which induces oxidative stress and inflammatory responses in cells. The fibroblasts/media were then analysed as described below immediately or snap frozen in liquid nitrogen and stored at −70° C. for future analysis.

Prostaglandin E2 (PGE2) assay Volumes of 50 μl culture medium were taken for PGE2 assay after gently shaking the culture plate. PGE2 levels in the medium were determined with a Biotrak PGE2 immunoassay kit (Amersham, UK). The assay is based on the competition between unlabelled PGE2 in the sample and a fixed quantity of horseradish peroxidase labelled PGE2 for a limited amount of fixed PGE2 specific antibody. Concentrations of unlabelled sample PGE2 are determined according to a standard curve which was obtained at the same time.

ICAM-1 assay Media were discarded and cells washed with Dulbecco PBS. To the washed cells, 150 μl 0.1% Triton X-100 (Sigma) was added for 3 minutes to extract ICAM from cell membrane. The extracts were transferred to Eppendoff centrifuge tubes and centrifuged at 1000 g for 2 min to remove cell debris. A volume of 100 μl supernatant was used for ICAM assay. The soluble ICAM-1 was assessed with commercially available immunoenzymometric assay kit (R&D Systems). Concentrations of ICAM-1 in the samples were determined based on parallelly running standard curve.

Results:

The below graph (FIG. 1) demonstrates that challenging cells with an inflammatory stimulus such as PMA (Phorbol myristyl acetate) causes an increase in the inflammatory response as measured by prostaglandin E2 (PGE2) production. Pinolenic acid, even at the levels of 10 ng/ml, dramatically reduces the inflammatory response as measured by PGE2 production. good anti-inflammatory activity.

EXAMPLES

1. Concentration of Pinolenic Acid by Hydrolysis of Pine Seed Oil 80 g of pine seed oil (Pinolenic acid: 16%) were mixed with 32 g of dest. water (40%). 400 mg (5%) of Candida rugosa lipase were added and the whole reaction mixture was shaken in shaker with 150 rpm at 40° C. After 1 ½ h the reaction was stopped by denaturing the lipase by heat. The reaction vessel was incubated in a water bath at 90° C. for 30 min. After separation of the two phases the oily phase was collected and used for further experiments.

For measuring the free fatty acid content 2 g of the sample was treated with 10 ml of isooctane to extract the fatty acids as well as the tri-, di-, and monoglycerides. After centrifugation for 5 min at 300 rpm the isooctane phase was evaporated by nitrogen.

The free fatty acid content was measured by titration with 0.2 N NaOH with phenolphthalein. The free fatty acid content was 74.4%.

To determine the concentration of pinolenic acid in the tri-, di-, and monoglyceride fraction the free fatty acids were separated by a silica amino propyl column. The fatty acid composition (high resolution FAME) was measured by GC with FID as detector. In the glyceride fraction pinolenic acid was enriched to 31.3%.

2. Concentration of Pinolenic Acid by Enzymatic Hydrolysis and Separation of the Glyceride Fraction by Short Path Distillation Six samples were prepared as following: 80 g of pine seed oil (Pinolenic acid: 16%) were mixed with 32 g of dest. water (40%). 400 mg (5%) of Candida rugosa lipase were added and the whole reaction mixture was shaken in shaker with 150 rpm at 40° C. After 1 ½ h the reaction was stopped by denaturing the lipase by heat. The reaction vessel was incubated in a water bath at 90° C. for 30 min. After separation of the two phases the oily phase was collected and used for further experiments. For measuring the free fatty acid content 2 g of the sample was treated with 10 ml of isooctane to extract the fatty acids as well as the tri-di-, and monoglycerides. After centrifugation for 5 min at 300 rpm the isooctane phase was evaporated by nitrogen. The free fatty acid content was measured by titration with 0.2 N NaOH with phenolphthalein. The free fatty acid content in all samples was between 70.8–76.4%. The free fatty acids were removed by short path distillation with the following conditions:

Distillation temperature: 180° C. Pressure: 2–3 $10^{-2}$

The glyceride fraction remains as residue.

The fatty acid composition (high resolution FAME) was measured by GC with a FID as detector. In the glyceride fraction pinolenic acid was enriched to 28.5%.

The residue has the following tri-, di-, and monoglyceride composition:

| | |
|---|---|
| Triglycerides: | 53.5% |
| Diglycerides: | 44.6 |
| Monoglycerides: | 0.3% |
| FFA | 1.6% |

Composition of the FFA distillate after SPD:

| | |
|---|---|
| Triglycerides: | 6.8% |
| Diglycerides: | 6.0 |
| Monoglycerides: | 1.9 |
| FFA | 85.3 |

3. Production of Enriched Pinolenic 100 g pine nut oil
100 g lauryl alcohol
100 g water
2g R. oryzae Stirred vessel at 30° C. for 70 minutes. 500 ml of hexane and 500 ml of water added. Phases allowed to separate. Organic phase washed with 2×200 ml of water followed by 100 ml of saturated sodium chloride solution. This was then dried over sodium sulphate and evaporated under reduced pressure using a rotary evaporator. The resulting oil was evaporated under reduced pressure at 145° C. using a short path evaporator to remove the pinolenic enriched free fatty acid and unreacted lauryl alcohol. This distillate was then evaporated again at 105° C. to remove the lauryl alcohol from the fatty acid.

| Fatty acid | % |
|---|---|
| C16:0 | 3.69 |
| C16:1 | 0.14 |
| C18:0 | 2.18 |
| C18:1  c9 | 11.43 |
| C18:1  c11 | 11.37 |
| C18:2 | 24.37 |
| PINOLENIC ACID | 39.8 |
| C20:0 | 0.4 |
| C20:1 | 0.66 |
| ? | 0.57 |
| ? | 0.48 |
| C20:2 | 4.16 |

4. Preparation of Different Blends with Pinolenic Acid Concentrate (free fatty acids, )

Blends were made of the following oils in the ratios indicated in the tables:

Borage oil with 20 wt % gamma linoleic acid: GLA B 20
A fish oil concentrate with 40 wt % polyunsatuted fatty acids: D 40 (Marinol)
A concentrate of conjugated linoleic acid: CLA.G.60
A concentrate of pinolenic acid: PAc
Sunflower oil: SF
An interesterified palm oil stearin/palmkernel stearin fat: INES
A palm mid fraction: nPOm The fatty acid composition of the fat components is:

| | Saturated fatty acids | Oleic + linoleic acid | trans fatty acids |
|---|---|---|---|
| GLA B 20 (Borage oil) | 15% | 54% | <10 |
| D 40 (Marinol) | 17% | 10% | <10 |
| CLA G 60 | 5.5% | 30% | 60% |
| Pac (Pinolenic acid concentrate, CH) | 6% | 35% | <10 |
| SF (sunflower oil) | 13% | 87% | — |
| INES NK | 90% | 8% | <2 |
| nPom | 63% | 36% | <1 |

Composition of the blends

| Blend A | B | B' | B" | N 20 | N 35 |
|---|---|---|---|---|---|
| 5 | 30% PAc | 20% D 40 | 30% nPOM | 20% SF | 4 | 0.2 |
| 6 | 50% PAc | 10% CLA G 60 | 30% INES | 10% SF | 18.5 | 6.9 |
| 7 | 40% PAc | 30% GLA 22 | 30% nPOM | | 3.6 | 0 |

Fatty acid Composition of the blends

| Blend | Saturated | Oleic + linoleic acid | Pinolenic acid |
|---|---|---|---|
| 5 | 26.7% | 40.7% | 12% |
| 6 | 31.9% | 29.1% | 20% |
| 7 | 25.8% | 41% | 16% |

5. Preparation of Different Blends with Pinolenic Acid Concentrate

Blends were made as described in example 4 using the same oils. Fatty acid composition of fat components Composition of the blends

| Blend A | B | B' | B" | N 20 | N 35 |
|---|---|---|---|---|---|
| 1 | 30% PAc | 20% D 40 | 30% nPOM | 20% SF | 3.9 | 0.1 |
| 2 | 50% PAc | 10% CLA G 60 | 30% INES | 10% SF | 22.3 | 9.2 |
| 3 | 40% PAc | 30% GLA 22 | 30% nPOM | | 3.2 | 0 |
| 4 | 40% PAc | 10% SF | 50% nPOM | | 11.7 | 0.2 |

Fatty acid Composition of the blends

| Blend | Saturated | Oleic + linoleic acid | Pinolenic acid |
|---|---|---|---|
| 1 | 29.4% | 43.7% | 8.4% |
| 2 | 33.8% | 37% | 14% |
| 3 | 27.4% | 45% | 11.2% |
| 4 | 36.8% | 44.7% | 11.2% |

6. Preparation of Margarine

Eight margarines were produced under the same process conditions.

a. Formulation

Aqueous Phase

| | |
|---|---|
| Water | 18.48% |
| Potassium Sorbate | 0.15 |
| Citric Acid | 0.07 |
| SMP | 1.0 |

Fat Phase

| | |
|---|---|
| Fat Blend | 80.0 |
| Hymono 8903 | 0.3 |

Fat Phase:

Product 1. 12% InEs, 88% SF (Control)

Product 2. 12% InEs, 10% Pine Nut Oil, 78% SF

Product 3. 12% InEs, 40% Pine Nut Oil, 48% SF

InEs=same as INES from example 4

SF=same as in example 4

Pine nut oil contained 16 wt % of pinolenic acid b. Process Conditions

The process line was configured as:

Premix - Pump - $A_1$-unit - $C_1$-unit - $A_2$-unit

Premix temperature was set at 60° C. and 60-rpm stirrer speed. All units were set to 15° C., with shaft speeds set to 1000 rpm. Throughput was 50 g/min. using the constant displacement pump.

For all products a premix was prepared by slowly adding the prepared aqueous phase to the oil phase in the premix tank. A 2kg-batch size was employed.

The mix was stirred for 15 minutes before pumping. After pumping, the line was allowed to run for 15 minutes before any collection of product.

The following process parameters were recorded:

| Product | $A_1$ exit (° C.) | $C_1$ exit (° C.) | $A_2$ exit (° C.) | Line Pressure (bar) |
|---|---|---|---|---|
| Control | 20.2 | 19.4 | 17.6 | 1.0 |
| 10% Pine Nut Oil | 20.5 | 19.6 | 17.6 | 1.1 |
| 40% Pine Nut Oil | 20.4 | 19.7 | 17.6 | 1.1 |

All tubs were placed at 5° C. After one day, one tub of each was transferred to each of 5°, 10°, 15° and 20° C. for evaluations after one week.

The spreads containing Pine Nut Oil were more yellow than standard spreads.

All samples spread easily with no apparent water loss.

All products are of excellent quality and displayed very good values for hardness (C-values), collar and conductivity at all storage temperatures (i.e. 5, 15 and 20° C.)

| Sample | C-Value (g/cm$^2$) | Collar (Scale I to VI) | Conductivity ($\mu$Scm$^{-1}$) |
|---|---|---|---|
| Control | 630 | I/II | <10$^{-5}$ |
| 10% Pine Nut Oil | 670 | I/II | <10$^{-5}$ |
| 40% Pine Nut Oil | 600 | I/II | <10$^{-5}$ |

7. Preparation of Ice Cream

TABLE 1

Recipe
The following recipe was applied (cf table 1)

| Component | Wt % |
|---|---|
| Fat blend | 10.0 |
| Skimmed milk powder | 10.0 |
| Crystal sugar | 12.0 |
| Clear syrup | 4.0 |
| Dextrose anhydrate | 2 |
| Dimodan PVP | 0.6 |
| Water | 61.4 |

The fat blends that were used are disclosed in table 2

TABLE 2

Fat blend

| Component | Wt % |
|---|---|
| POf iv65 | 30 |
| CN | 20 |
| SF | 50 |

The sugar, milk powder and dextrose were mixed and added to the water. The mixture was heated to 70° C. and the clear syrup was added. Next the fat blend and the emulsifier was added. The emulsion was stirred with an ultra-turrax, cooled down to 20° C. and stirred again with the ultra-turrax. The emulsion stayed overnight in the refrigerator at 7° C. The batch ice cream machine was held for 24 hours at −28° C. The emulsion was stirred in the machine for 40 minutes until the temperature was at its lowest. The resulting ice cream was stored at −18° C. for at least 3 days and was then evaluated.

In a composition according to the invention the 50% SF was replaced by 50% pine oil, containing 16 wt % of pinolenic acid. This resulted in products with the properties as given in table 3.

From this table it can be concluded that the products according to the invention displayed a better hardness and a higher overrun.

TABLE 3

| | Reference | Pinolenic acid |
|---|---|---|
| Overrun in % | 6.7 | 18.5 |
| Mouthfeel | | Good |
| hardness | 52 | 95 |

8. Preparation of a Filling

The following recipe was applied:

TABLE 4

Recipe of the filling

| Component | Wt % |
|---|---|
| Fat blend | 35.0 |
| Cocoa powder | 10.0 |
| Skimmed milk powder | 7.0 |
| Sugar | 48.0 |
| Lecithin | 0.5 |

The following fat blends were used:

| 1. | 40/10/50 | CCBs/POfiv65/SF (reference) |
|---|---|---|
| 2. | 40/10/50 | CCBs/POfiv65/Pine oil concentrate (28.5 % pinolenic acid) |
| 3. | 40/10/50 | CCBs/POfiv65/Pine oil |

CCBs being a stearin fraction of cocoa butter PofIV65 being an olein fraction of palm oil with an iodine value of 65

All the components of the recipe were mixed in a porcelain bowl at a temperature of 55° C. The particles of the mixture were minimised by the use of a mortar. The mixture was cooled to 29° C. before depositing in aluminium cups.

Hardness was measured by using the Stevens Texture Analyser (STA) after 3 days at 20° C., cone 60°, penetration 2 mm:

| Number | Fat type | STA (g) |
|---|---|---|
| 1 | 40/10/50 CCBs/POfiv65/SE (reference) | 364 |
| 2 | 40/10/50 CCBs/POfiv65/Pine oil concentrate | 369 |
| 3 | 40/10/50 CCBs/POfiv65/Pine oil | 307 |

From this table it can be concluded that the filling with pilolenic acid concentrate has an hardness equivalent to the harness of the reference, while the pine seed oil without further enrichment is slightly softer.

What is claimed is:

1. A concentrate comprising 28 to 60 wt % of pinolenic acid, 10 to 60 wt % of linoleic acid, 5 to 52 wt % of oleic acid, wherein the trans plus saturated fatty acid content of said concentrate is less than 10 wt %.

2. The concentrate according to claim 1, wherein the pinolenic acid and other fatty acids are present as free acids and/or in the form of mono- and/or di- and/or triglycerides.

3. A composition comprising the concentrate according to claim 1, further comprising at least one glyceride component selected from glycerides comprising linoleic acid and/or oleic acid and/or trans acids and/or saturated fatty acids, said concentrate and glyceride being present in such ratios that the final concentrate within the composition contains:

0 to 70 wt % trans plus saturated fatty acids, 1.5 to 60 wt % of pinolenic acid, and 25 to 85 wt % of linoleic plus oleic acids.

4. A composition according to claim 3 wherein the said concentrate displays a solid fat content, as measured by NMR-pulse on non-stabilized fats, of:

N20: 1–80 and

N35: less than 20.

5. A composition according to claim 3 wherein the glyceride component is selected from the group consisting of:

(i) soybean oil, sunflower oil, rape seed oil, and cotton seed oil;

(ii) cocoa butter or cocoa butter equivalent;

(iii) palm oil or fractions thereof; and (iv) hardened liquid oils; or (v) mixtures of one or more of components (i) to (iv).

6. A composition according to claim 3 wherein the trans content in the final concentrate is less than 10 wt %.

* * * * *